US009155596B2

(12) United States Patent
Moessle

(10) Patent No.: US 9,155,596 B2
(45) Date of Patent: Oct. 13, 2015

(54) MANUAL DEVICE FOR DISPENSING A PASTY FILLER

(75) Inventor: Walter Moessle, Mittelbiberach (DE)

(73) Assignee: KALTENBACH & VOIGT GMBH, Biberach (DE)

( * ) Notice: Subject to any disclaimer, the term of this patent is extended or adjusted under 35 U.S.C. 154(b) by 0 days.

(21) Appl. No.: 13/256,305

(22) PCT Filed: Mar. 12, 2010

(86) PCT No.: PCT/EP2010/053173
§ 371 (c)(1),
(2), (4) Date: Oct. 28, 2011

(87) PCT Pub. No.: WO2010/103099
PCT Pub. Date: Sep. 16, 2010

(65) Prior Publication Data
US 2012/0104050 A1    May 3, 2012

(30) Foreign Application Priority Data

Mar. 13, 2009   (DE) .......................... 10 2009 013 000

(51) Int. Cl.
| | | |
|---|---|---|
| *A61C 1/07* | (2006.01) | |
| *A61C 5/06* | (2006.01) | |
| *B05C 17/01* | (2006.01) | |
| *B05C 17/015* | (2006.01) | |

(52) U.S. Cl.
CPC . *A61C 5/062* (2013.01); *A61C 1/07* (2013.01); *B05C 17/01* (2013.01); *B05C 17/015* (2013.01); *B05C 17/0116* (2013.01)

(58) Field of Classification Search
CPC ............ A61C 1/07; A61C 5/062; A61C 5/04; B05C 17/01; B05C 17/0116

USPC ...................... 433/80–90, 118; 222/325–327, 222/567–570; 604/82–92
See application file for complete search history.

(56) References Cited

U.S. PATENT DOCUMENTS

| | | | | |
|---|---|---|---|---|
| 4,405,249 | A * | 9/1983 | Scales ............................. | 606/93 |
| 4,820,152 | A * | 4/1989 | Warrin et al. .................... | 433/86 |
| 4,961,698 | A * | 10/1990 | Vlock ............................. | 433/86 |
| 4,993,947 | A * | 2/1991 | Grosrey .......................... | 433/81 |

(Continued)

FOREIGN PATENT DOCUMENTS

| | | |
|---|---|---|
| DE | 10001513 A1 | 4/2001 |
| DE | 102007022205 A1 | 11/2008 |

(Continued)

OTHER PUBLICATIONS

International Search Report for PCT/EP2010/053173 dated Apr. 10, 2010.

*Primary Examiner* — Cris L Rodriguez
*Assistant Examiner* — Mirayda A Aponte
(74) *Attorney, Agent, or Firm* — Marshall, Gerstein & Borun LLP

(57) ABSTRACT

A manual device, in particular for dental use, for dispensing a pasty filler, may reduce the viscosity of the filler by the introduction of vibrational energy. The device may include a device housing, a detachable container for the pasty filler that includes an outlet nozzle at a front end thereof, a vibration generator with an oscillating body, and pressure generating means for exerting pressure on the pasty filler, wherein the oscillating body is detachably connected to the container in a middle region thereof.

16 Claims, 1 Drawing Sheet

(56) References Cited

U.S. PATENT DOCUMENTS

| | | | |
|---|---|---|---|
| 5,125,836 A * | 6/1992 | Dragan et al. | 433/90 |
| 5,267,859 A * | 12/1993 | Discko, Jr. | 433/89 |
| 5,306,147 A * | 4/1994 | Dragan et al. | 433/90 |
| 5,489,207 A * | 2/1996 | Dragan et al. | 433/90 |
| 5,743,431 A * | 4/1998 | Brattesani | 222/1 |
| 5,743,436 A * | 4/1998 | Wilcox et al. | 222/137 |
| 5,853,290 A * | 12/1998 | Winston | 433/86 |
| 5,893,714 A * | 4/1999 | Arnold et al. | 433/90 |
| 6,116,702 A * | 9/2000 | Maehara | 303/116.1 |
| 6,340,299 B1 * | 1/2002 | Saito | 433/80 |
| 6,616,448 B2 * | 9/2003 | Friedman | 433/32 |
| 6,790,037 B1 * | 9/2004 | Orecchia | 433/90 |
| 7,014,462 B1 * | 3/2006 | Tilse | 433/90 |
| 7,086,861 B2 * | 8/2006 | Pitz et al. | 433/90 |
| 7,108,509 B2 * | 9/2006 | Heesen | 433/90 |
| 7,344,375 B2 * | 3/2008 | Mukasa et al. | 433/90 |
| 7,604,479 B2 * | 10/2009 | Buchanan | 433/119 |
| 7,857,621 B2 * | 12/2010 | Teufelberger et al. | 433/29 |
| 2003/0165793 A1 * | 9/2003 | Yobel et al. | 433/90 |
| 2004/0126733 A1 * | 7/2004 | Ronvig | 433/90 |
| 2004/0248058 A1 * | 12/2004 | Hahn et al. | 433/29 |
| 2005/0241666 A1 * | 11/2005 | Bodet et al. | 134/1 |
| 2006/0106363 A1 * | 5/2006 | Aravena et al. | 604/506 |
| 2008/0118887 A1 * | 5/2008 | Teufelberger et al. | 433/29 |
| 2008/0206706 A1 * | 8/2008 | Mossle | 433/118 |
| 2009/0004625 A1 * | 1/2009 | Esposti et al. | 433/165 |
| 2009/0042163 A1 * | 2/2009 | Johnson | 433/86 |
| 2009/0191506 A1 * | 7/2009 | Clark | 433/41 |
| 2010/0304322 A1 * | 12/2010 | Emde | 433/25 |
| 2011/0098633 A1 * | 4/2011 | Kurrek et al. | 604/22 |
| 2011/0117518 A1 * | 5/2011 | Pond | 433/89 |
| 2011/0143305 A1 * | 6/2011 | Wagner et al. | 433/29 |
| 2012/0258423 A1 * | 10/2012 | Dubey et al. | 433/90 |

FOREIGN PATENT DOCUMENTS

| | | |
|---|---|---|
| WO | WO-2006136398 A2 | 12/2006 |
| WO | WO 2006136398 A2 * | 12/2006 |

\* cited by examiner

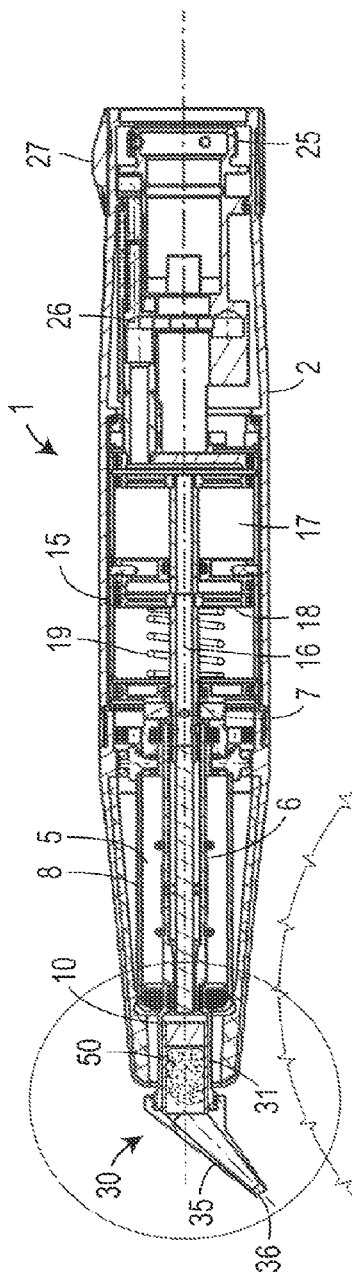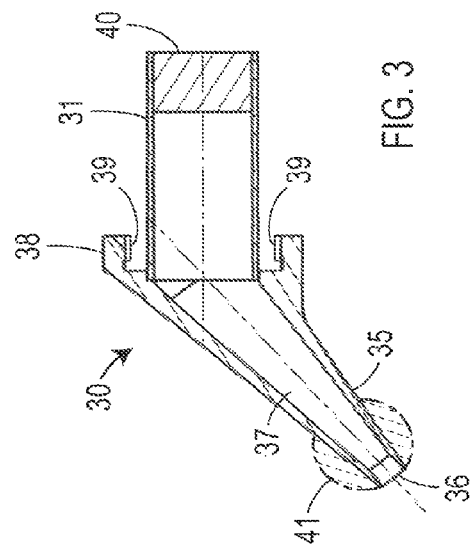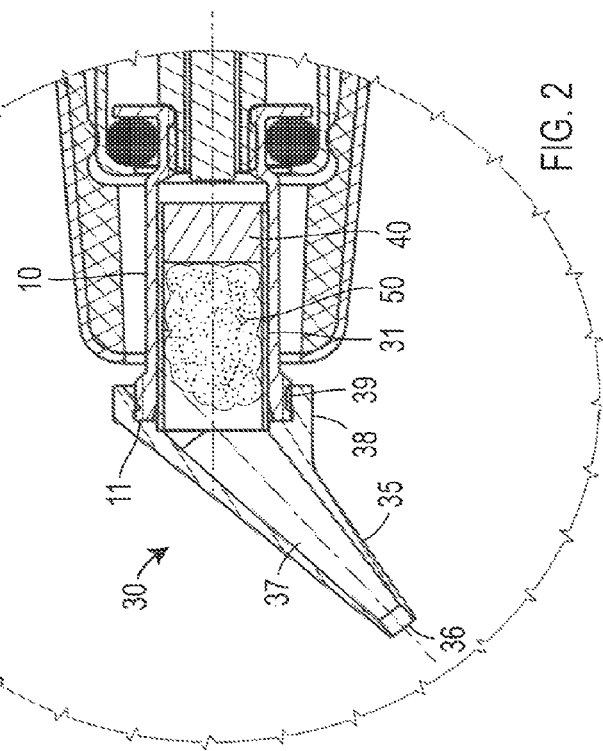

MANUAL DEVICE FOR DISPENSING A PASTY FILLER

BACKGROUND OF THE INVENTION

1. Field of the Invention

The present invention relates to a handheld tool which is provided in particular for dental purposes and is designed to dispense a pasty filling material, the viscosity of which can be reduced by supplying oscillation energy. Furthermore, the present invention relates to a container for accommodating a pasty filling material, which can be used in such a handheld tool.

2. Related Technology

In medical technology, it is known to fill, and thus to repair, cavities in an animal or human body part or in a prosthesis with a filling material, for example after a defect has been eliminated by removal of material. For this purpose, use is made of curable filling materials, which are introduced into the cavity in a pasty or liquid state and then cure. In this case, a distinction should be made between a direct filling and an indirect filling. In a direct filling, only the filling material is introduced into the cavity so that it fills the cavity. In an indirect filling, a preferably matching inlay insert containing the filling material is inserted into the cavity so that the inlay insert connects the insert to the wall of the cavity. In this case, not only mechanical anchoring of the filling material in the cavity is important, but also sealed accommodation of the filling material in the cavity, in order to avoid gaps which can be passed through by contamination and germs, which can lead to inflammation in a body tissue and can destroy the preparation.

A typical application of an above-described preparation, in which there are particular requirements with regard to the handheld tool and the handling thereof, is tooth preparation in the oral cavity of a patient or in a practice head for learning purposes. In such a dental treatment case, there are particular requirements with regard to the structural size of the handpiece, since the oral cavity of a patient is comparatively small and therefore, with necessary visibility being taken into account, a structural size which is as small as possible should be sought.

DE 100 01 513 A1 describes a method for filling a synthetic resin-based tooth filling material into a cavity of a tooth and a handheld tool for carrying out such a method, wherein, during filling, the filling material and a nozzle of the handheld tool are acted on with sound, in particular with ultrasound, and the handheld tool has means which convey the filling material out of a storage container in the nozzle. This known method and handheld tool make it possible to use filling materials having a comparatively high content of fillers, which increase the viscosity of the filling material and thus reduce shrinkage and the risk of gaps forming during curing. In this previously known handheld tool, there is provided a lever device for conveying the filling material, and when this lever device is manually actuated an ultrasound source, in particular a piezoelectric oscillator, is switched on at the same time, this ultrasound source or piezoelectric oscillator being arranged in the rear region of the body of the handheld tool. The filling material is arranged in a cartridge, which can be inserted into a cutout arranged in the front end region of the body of the handheld tool and fixed therein. When the lever device is manually actuated, the filling material is conveyed out by a feed ram which is connected to the lever device and acts on the rear end of the cartridge.

A comparable tool is also known from WO 2006/13639 A2 of the applicant. In this case, particular modifications to the handheld tool are proposed, which help to improve both the dispensing of the composite material and also the handling of the tool.

For reasons of hygiene, it would be advantageous to configure the storage container for the composite material with the outlet nozzle in the form of a cartridge, as a disposable or single-use article. For each treatment, a new cartridge could then be used, so that cleaning and disinfection, which would otherwise be essential, can be avoided. On the other hand, the result of this solution is that a detachable connection is necessary between the storage container and the handheld tool, and this can lead to problems with regard to the effectiveness of oscillation transmission and with the dispensing of the filling material.

SUMMARY OF THE INVENTION

It is therefore the object of the present invention to optimize the concepts, known from the prior art, for dispensing a filling material, in order ultimately to open up the possibility of designing the storage container for the pasty filling material in a detachable or exchangeable manner, wherein nevertheless effective oscillation transmission and dispensing of the material should be ensured.

Accordingly, the invention provides a handheld tool, in particular for dental purposes, for dispensing a pasty filling material, the viscosity of which can be reduced by supplying oscillation energy, the tool having a tool housing, a detachable container for the pasty filling material that has an outlet nozzle at its front end, an oscillation generator having an oscillating body, and pressure-generating means for exerting pressure on the pasty filling material, wherein the oscillating body is detachably connected to the container in a central region of the container.

In this case, according to a first aspect of the present invention, it is first of all provided that the container for the pasty filling material is configured so that it is detachably connected in a central region to an oscillating body of the handheld tool.

According to this first aspect, there is accordingly proposed a handheld tool, in particular for dental purposes, for dispensing a pasty filling material, the viscosity of which can be reduced by supplying oscillation energy, having a tool housing, a detachable container for the pasty filling material, the container having an outlet nozzle at its front end, an oscillation generator having an oscillating body, and pressure-generating means for exerting pressure on the pasty filling material, wherein, according to the invention, the oscillating body is detachably connected to the container in a central region of the latter.

Furthermore, according to this first aspect of the present invention, there is also proposed a container for use with a handheld tool as described above, wherein the container is designed to accommodate a pasty filling material and has at its front end an outlet nozzle. According to the invention, it is provided that the container has in its central region means for detachably connecting it to the handheld tool.

As is described in more detail in the following text, the configuration according to the invention of the container for the filling material ensures that the oscillations of the oscillating body are transmitted more effectively to the container and accordingly the viscosity can be reduced more effectively when the filling material is dispensed.

In this case, according to an advantageous development of the invention, it is provided that the oscillating body is connected to the container via a quick-action connection, in particular via a screw connection or a bayonet connection.

This enables easy fastening and detachment of the container to and from the hand-held tool.

In this case, the container may have in its front region a cannula which forms the outlet nozzle, wherein in this case the means for connecting the container to the oscillating body are formed in particular at the end of the cannula. This ensures that the oscillations are transmitted effectively to the filling material up to the time at which the pasty filling material leaves the cannula. Preferably, the cannula in this case forms a separate component which is joined together to form the container with a further component that forms an accommodating chamber for the filling material. This further component that forms the accommodating chamber for the filling material can then be arranged, in particular in a state arranged on the handheld tool, with a perfect fit substantially within an accommodating opening in the oscillating body. The further component thus serves for guidance and for improved introduction of the optionally used thread for detachably fastening the container to the handheld tool. Furthermore, the wall of the container no longer has to be formed to be stable under pressure, since it can now be supported directly on the oscillating body and thus absorbs all the forces.

The two-part form of the container is furthermore advantageous since it makes it possible to form the cannula in an effective and thus cost-effective manner. The cannula is in this case formed in particular in such a way that it has a conical clearance which is directed towards the front end. The effect of this clearance is that, during dispensing, the filling material is continuously subjected to shear stress, and the result of this is that it is heated through more effectively and thus becomes more fluid. This contributes to even further improved dispensing of the material.

Furthermore, the container may have in its rear region a pressure piston, on which pressure-generating means of the handheld tool act to dispense the filling material. The pressure-generating means may in this case have a piston rod which acts on the pressure piston.

In this case, according to a second aspect of the present invention it is furthermore possible for provision to be made of restoring means, in particular one or more spring elements, with the aid of which the piston rod is prestressed into a starting position. Following a change of the container holding the filling material, the tool is thus immediately ready for use again. The oscillation generator is preferably a pneumatically drivable oscillation generator, wherein in this case a common pressure supply for the oscillation generator and the pressure-generating means is then provided.

According to the second aspect of the present invention, there is accordingly proposed a handheld tool, in particular for dental purposes, for dispensing a pasty filling material, the viscosity of which can be reduced by supplying oscillation energy, having a tool housing, a detachable container for the pasty filling material, said container having an outlet nozzle at its front end, an oscillation generator having an oscillating body, and pressure-generating means for exerting pressure on the pasty filling material, wherein, according to the invention, the container has in its rear region a pressure piston and the pressure-generating means have a piston rod which acts on the pressure piston in the container, and wherein furthermore restoring means, in particular one or more spring elements, for prestressing the piston rod into a starting position are provided.

As already explained above, the automatic restoring of the piston rod leads to improved handling of the tool, since when the storage container is changed no further activities are required in order to put the handheld tool into the operating state. This, too, leads to it being possible for the storage container to be used in an easier and more effective manner as a single-use article.

Viewed overall, the present invention accordingly specifies an improved concept for dispensing filling material in order to produce tooth fillings, wherein in particular the possibility of configuring the storage container for the filling material having the outlet nozzle as a single-use or disposable article is opened up.

BRIEF DESCRIPTION OF THE DRAWINGS

The invention will be explained in more detail in the following text on the basis of the accompanying drawing, in which:

FIG. 1 shows the overall view of a handheld tool according to the invention in a lateral sectional illustration;

FIG. 2 shows an enlarged view of the front end region of the handheld tool with the container for the composite material fastened thereto; and FIG. 3 shows the container for the composite material in a sectional illustration.

DETAILED DESCRIPTION

The handheld tool according to the invention, which is designated overall by the reference number 1 in the Figures, has an elongate, in particular rod-shaped, tool shaft 2, which is configured in a tube-like manner to accommodate the various components of the tool 1. In this case, an oscillation generator 5 is arranged in particular in the front region of the tool shaft 2 and is coupled via oscillation transmission means to a cartridge 30, which will be described in more detail hereinbelow. The cartridge 30 serves to accommodate and dispense a filling material 50, which can be liquefied by being subjected to oscillations in the audible sound or ultrasound range.

The handheld tool 1 furthermore supports the dispensing of the filling material 50 located in the cartridge 30, for which purpose pressure-generating means 15 are formed in the central region of the tool shaft 2. These pressure-generating means 15, which will be described in more detail hereinbelow, have in particular a piston rod 16 which, during operation of the handheld tool 1, exerts pressure on a piston 40 located in the rear region of the cartridge 30, as a result of which the material 50 located in the cartridge 30 is conveyed to the front outlet opening 36 in an outlet nozzle 35.

A common pressure supply is provided for the oscillation generator 5 and for the pressure-generating means 15. The handheld tool 1 is for this purpose first of all equipped in its rear end region with a coupling part 25, which allows the connection of the tool 1 to a hose which is known per se and leads to a supply unit (not illustrated). The coupling piece 25 can in this case be configured in such a way that the handheld tool 1 is allowed to rotate freely with respect to the supply hose.

The pressure of the compressed air made available by the supply hose is in this case first of all regulated via a pressure limiter 26 arranged in the rear region of the shaft 2. This pressure limiter 26 is set via an operating element 27, for example a setting ring, which is formed on the outer circumference of the handheld tool 1. By rotating this setting ring 27, the pressure can be increased or reduced as desired, and thus the performance of the oscillation generator 5 and of the pressure-generating means 15 can be set. The pressure limiter 26 furthermore ensures that pressure fluctuations that arise in the air supply are equalized, so that a uniform working pressure is permanently provided.

The compressed air, which is set by the pressure limiter 26 to a desired pressure, is then first of all directed via a piston chamber 17 of the pressure-generating means 15 into the front region of the handheld tool 1. Within this piston chamber 17 there is arranged a piston 18, which is connected to the piston rod 16 and is formed in particular as a double piston. The use of a double piston increases the pressure force on account of the application area for the compressed air, increased hereby, so that ultimately the piston rod 16 is pushed forward with sufficient force. Furthermore, a spring 19 is arranged in the front region of the piston chamber 17, this spring 19 being supported both on the front end wall of the piston chamber 17 and on the piston 18. This spiral spring 19 serves as a restoring aid and ensures that after the handheld tool 1 has been switched off, and thus the compressed air has been interrupted, the piston 18 and the piston rod 16 connected to the piston 18 are moved automatically into a starting position. Manual restoring of the piston rod 16 is accordingly not necessary, and so once a new cartridge 30 has been installed on the tool 1, the latter is automatically ready for use.

The compressed air is furthermore also supplied to the oscillation generator 5, which is a pneumatic oscillation exciter, configured in a known manner, for generating oscillations in the audible sound or ultrasound range. The oscillation exciter has a resonant body 6, which is mounted in an elastic manner and supported at its front and rear ends. Furthermore, the resonant body is mounted via appropriate means 7 in the shaft of the tool 1 so that it cannot rotate and is configured in such a way that it is made to oscillate when compressed air is supplied. The resonant body 6 is in this case arranged within a chamber formed by a tube 8, being in turn at a distance from an outer wall of the shaft 2. This allows noise damping during the operation of the oscillation generator 5.

Furthermore, the resonant body 6 is configured as a hollow body, so that the piston rod 16 is guided axially through it. At its front end, the resonant body 6 is coupled to a tube-like oscillating body 10, via which—as is described in more detail hereinbelow—the oscillations are then transmitted to the cartridge 30.

Once the handheld tool has been activated, the oscillation generator 5 accordingly causes the oscillating body 10 to vibrate. At the same time, the pressure-generating means 15 push the piston rod 16 forward, i.e. to the left in the illustrated case, in order to support the dispensing of the composite material 50. It is thus not necessary to actuate the tool 1 separately in order to dispense the filling material 50.

In the following text, the cartridge 30 will be described in detail, this cartridge 30 being intended to be configured in particular as a disposable article. It consists preferably of two elements, a front outlet nozzle 35 and a tube-like component 31, which serves as an accommodating container for the composite material 50. The accommodating container 31 is configured in a hollow-cylindrical manner and is coupled at its front end to the outlet nozzle 35, for example is welded or adhesively bonded thereto or is connected thereto by a press fit. Arranged in a movable manner at the rear end of the accommodating container 31 is a piston 40, which is pushed forward via the piston rod 16 in order to dispense the filling material 50.

For ergonomic reasons, the outlet nozzle 35 is arranged in an angled manner with respect to the container 31. It has an elongate cavity 37, which opens at its front end into the outlet opening 36. The elongate cavity 37 is in this case configured in particular in a conical manner, i.e. has a cross section that narrows increasingly in the direction of the outlet opening 36. The result of this is that, while it is being dispensed, the composite material 50 is continuously subject to shear stress and thus is heated through and liquefied more effectively. Compared to known solutions, in which outlet nozzles or cannulas usually have a cylindrical through-passage opening, improved liquefaction of the composite material 50 during the dispensing phase is accordingly achieved. In this case—as is indicated in FIG. 3—the front end of the outlet nozzle or cannula 35 can also be designed in the form of a spherical end region 41. In this case, the outlet nozzle 35 can be used to compact the material already introduced into the tooth cavity by operating the spherical end region 41 that is acted on by sound.

As can furthermore be gathered from the illustrations in FIGS. 2 and 3, the nozzle 35 has at its rear end facing the storage container 31 a flange-like end region 38, which is spaced apart slightly from the outer circumference of the storage container 31. Formed on the inner circumference of the flange-like end region 38 is a thread 39, via which the cartridge 30 can be screwed onto the oscillating body 10, which in turn has a thread 11, so that the configuration illustrated in FIG. 2 is achieved. In this case, it should be noted that, as an alternative to the screw connection illustrated, the cartridge 30 could also be attached to the tool 1 via a bayonet connection or some other suitable quick-action connection. The arrangement of the connecting means in the central region of the cartridge 30 leads to a number of advantages, which will be explained in the following text.

Thus, first of all it is ensured that, on account of the direct coupling of the nozzle 35 to the oscillating body 10 or the arrangement of the thread 39 at the rear end of the outlet nozzle 35, more targeted action of sound in order to liquefy the composite material 50 is achieved. It is in particular ensured that the sound can act on the composite material 50 virtually over the entire section, with in particular the reduction in the cross section contributing thereto, since the material 50 comes fully into contact with the wall of the outlet nozzle 35. Since, furthermore, the storage container 31 is located as far as possible within the oscillating body 10, a smaller region of the surface of the cartridge 30 is in contact with the outer side, and so a noise reduction during operation is achieved. Furthermore, it is not necessary for the wall of the container 31 to be formed in a manner stable under pressure, since it can now be supported directly on the oscillating body 10 and thus absorbs all the pressure forces.

Finally, these advantages lead to it being possible for the cartridge 30 to be configured in a simple manner as a disposable or single-use product. Hygiene regulations, in particular in dental practice, can be complied with out great effort, it being ensured at the same time, however, that the composite material is liquefied effectively during dispensing. This leads to a clear improvement in the operating properties of the handheld tool according to the invention.

In this case, it should be mentioned, in conclusion, that the cartridge according to the invention could of course also be used in handheld tools which do not have means for automatically dispensing the filling material but rather have, for example, a lever mechanism to be actuated separately, as is known from DE 100 01 513 A1. In this case, too, the particular arrangement of the cartridge on the tool contributes to an improved transmission of oscillations.

The invention claimed is:

1. A handheld tool for dispensing a pasty filling material, the viscosity of which can be reduced by supplying oscillation energy, the tool having:

a tool housing, a detachable container for pasty filling material, the container having an outlet nozzle at a front end, an oscillation generator having a tube-like oscillating body, and means for exerting pressure on the pasty filling material, the means being guided axially through the tube-like oscillating body, wherein:

the oscillating body is detachably connected rigidly to the container in a central region of the container via a quick-action connection including at least one of a screw connection and a bayonet connection, and the container has in a front region a cannula which forms the outlet nozzle, wherein the quick-action connection is formed at an end of the cannula.

2. The handheld tool of claim 1, wherein the cannula is a separate element which is joined together to form the container with a component that forms an accommodating chamber for the filling material.

3. The handheld tool of claim 2, wherein the component that forms the accommodating chamber for the filling material is arranged, in a state arranged on the handheld tool, substantially within an accommodating opening in the oscillating body.

4. The handheld tool of claim 1, wherein the outlet nozzle has a conical chamber which is directed toward the front end and through which the filling material is channeled.

5. The handheld tool of claim 1, wherein the container has in a rear region a pressure piston, on which the means for exerting pressure on the pasty filling material acts to dispense the filling material.

6. The handheld tool of claim 5, wherein the means for exerting pressure on the pasty filling material has a piston rod which acts on the pressure piston in the container.

7. The handheld tool of claim 6, wherein the container has a means for pre-stressing the piston rod into a starting position.

8. The handheld tool of claim 7, wherein the means for pre-stressing the piston rod into the starting position comprises one or more spring elements.

9. The handheld tool of claim 1, wherein the oscillation generator is a pneumatically drivable oscillation generator, wherein a common pressure supply for the oscillation generator and the means for exerting pressure on the pasty filling material is provided.

10. A container for use with a handheld tool for dispensing a pasty filling material, the viscosity of which can be reduced by supplying oscillation energy, wherein the container is designed to accommodate pasty filling material and has at a front end an outlet nozzle for dispensing the filling material, wherein the container has, in a central region of the container, means for detachably connecting the container directly to a tube-like oscillating body of the handheld tool, the means for detachably connecting the container to the oscillating body including at least one of a screw connection and a bayonet connection, wherein the container has in a rear region a pressure piston for exerting pressure on the pasty filling material, the pressure piston being guided axially through the tube-like oscillating body, and wherein the container has at a front end a cannula which forms the outlet nozzle, wherein the means for connecting the container to the handheld tool is formed at the end of the cannula.

11. The container of claim 10, wherein the means for detachably connecting the container to the handheld tool comprises a quick-action connection.

12. The container of claim 10 wherein the outlet nozzle has a conical chamber which is directed toward the front end and through which the filling material is channeled.

13. The container of claim 10, wherein the means for detachably connecting the container to the handheld tool is a quick-action screw connection or a quick-action bayonet connection.

14. A container for use with a handheld tool for dispensing a pasty filling material, the viscosity of which can be reduced by supplying oscillation energy, wherein the container is designed to accommodate pasty filling material and has at a front end an outlet nozzle for dispensing the filling material, wherein the container has, in a central region of the container, means for detachably connecting the container directly to a tube-like oscillating body of the handheld tool, the means for detachably connecting the container to the oscillating body including at least one of a screw connection and a bayonet connection, wherein the container has in a rear region a pressure piston for exerting pressure on the pasty filling material, the pressure piston being guided axially through the tube-like oscillating body, wherein the container has at a front end a cannula which forms the outlet nozzle, wherein the means for detachably connecting the container to the handheld tool is formed at the end of the cannula, and wherein the cannula is a separate element from the container and is joined to the container to form a component that forms an accommodating chamber for the filling material.

15. A handheld tool for dispensing a pasty filling material, the viscosity of which can be reduced by supplying oscillation energy, having a tool housing, a detachable container for pasty filling material having an outlet nozzle at a front end, an oscillation generator having a tube-like oscillating body, and means for exerting pressure on the pasty filling material, the means being guided axially through the tube-like oscillating body, wherein the container has in a rear region a pressure piston and the means for exerting pressure on the pasty filling material has a piston rod which acts on the pressure piston in the container, wherein means for pre-stressing the piston rod into a starting position are provided, wherein the oscillating body is directly connected to the detachable container via a quick-action connection including one or more of a screw connection and a bayonet connection, and wherein the container has in a front region a cannula which forms the outlet nozzle, wherein the quick-action connection is formed at an end of the cannula.

16. The handheld tool of claim 15, wherein the means for pre-stressing the piston rod into a starting position comprises one or more spring elements.

* * * * *